(12) United States Patent
Vason

(10) Patent No.: US 8,156,857 B2
(45) Date of Patent: Apr. 17, 2012

(54) EQUIPMENT FOR THE REHYDRATION OF YEASTS, IN PARTICULAR FOR OENOLOGY

(75) Inventor: Albano Vason, San Pietro in Cariano (IT)

(73) Assignee: Enologica Vason S.R.L., Pedemonte VR (IT)

( * ) Notice: Subject to any disclaimer, the term of this patent is extended or adjusted under 35 U.S.C. 154(b) by 712 days.

(21) Appl. No.: 12/237,096

(22) Filed: Sep. 24, 2008

(65) Prior Publication Data

US 2009/0078124 A1 Mar. 26, 2009

(30) Foreign Application Priority Data

Sep. 24, 2007 (IT) .............................. PD2007A0309

(51) Int. Cl.
*C12M 1/26* (2006.01)
*A23J 1/00* (2006.01)
(52) U.S. Cl. ................. 99/276; 99/278; 99/536; 99/516
(58) Field of Classification Search .................... 99/348, 99/516, 536, 276, 277, 278
See application file for complete search history.

(56) References Cited

U.S. PATENT DOCUMENTS

| 2003/0106437 A1* | 6/2003 | Pajunen et al. ................. 99/511 |
| 2003/0145735 A9* | 8/2003 | Francia ............................ 99/276 |
| 2004/0149137 A1* | 8/2004 | Francia ............................ 99/276 |
| 2004/0213889 A1* | 10/2004 | Dulau et al. .................. 426/656 |

FOREIGN PATENT DOCUMENTS

| EP | 1167514 A | 1/2002 |
| FR | 2710073 A | 3/1995 |

OTHER PUBLICATIONS

Ferrarini et al.,"Mechanical Dispersion Procedures Improve the Rehydration of Active Dry Yeast," Enzyme and Microbial Technology, 2007, pp. 0141-0229, vol. 40 No. 5.

* cited by examiner

*Primary Examiner* — Reginald L Alexander
(74) *Attorney, Agent, or Firm* — Browdy and Neimark, PLLC

(57) ABSTRACT

Equipment for yeast rehydration, in particular in dry, moist or in liquid dispersion form, which comprises a containment tank (2) closed by a cover (70) intended to receive a measured dose of yeasts to be rehydrated; first and second supply means (3, 4) adapted to respectively insert a rehydration liquid and nutritive substances in the tank (2); a circulation duct (14) placed in connection between at least one outlet opening (15) and at least one return opening (16, 16') of the containment tank (2), intercepted by pumping means (17) for making the fluid mixture flow between the openings (14, 16). The equipment comprises means for insufflating air (32) inside the tank (2) susceptible for creating an over-pressure of a value that is regulated through suitable vent means (18).

15 Claims, 1 Drawing Sheet

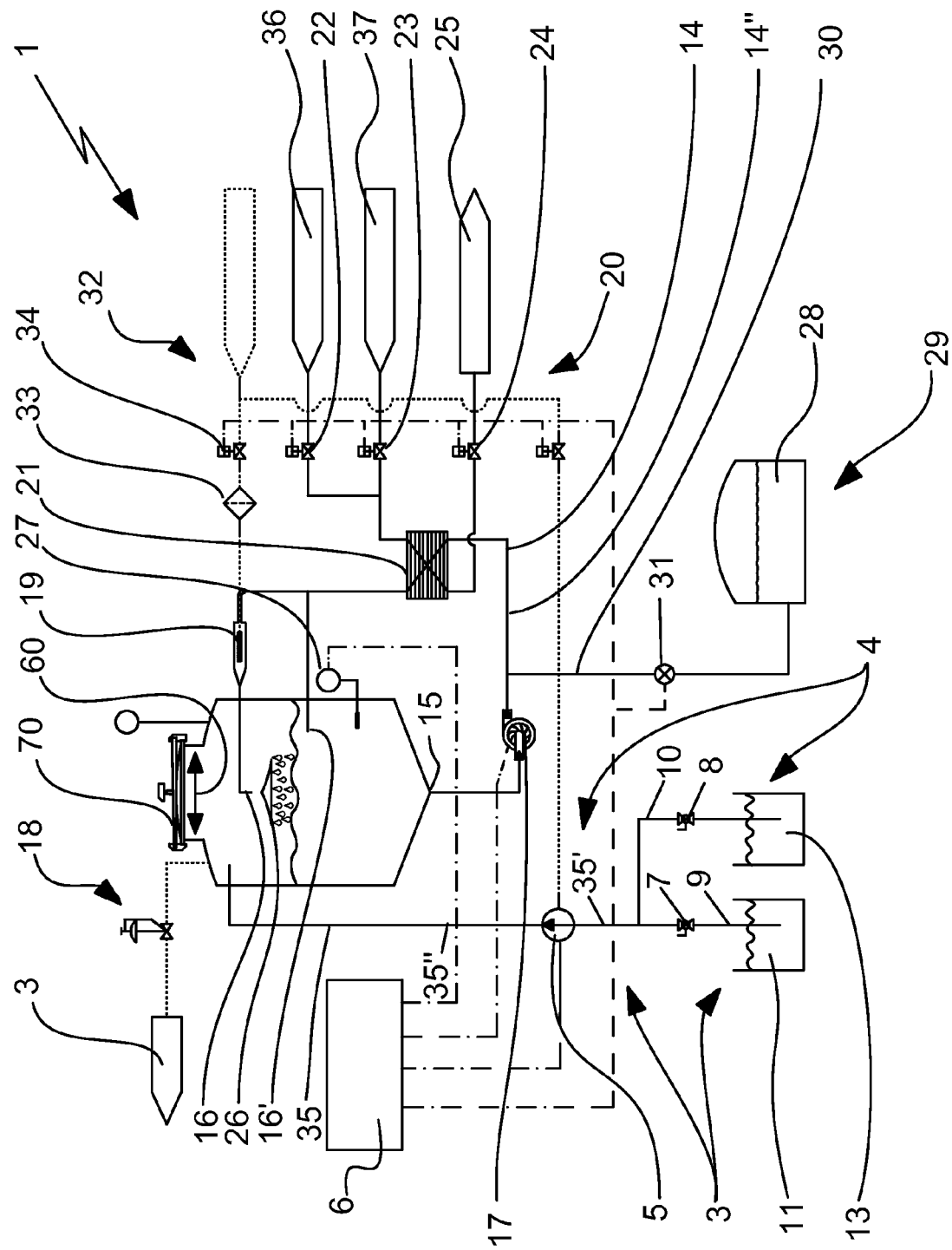

_US 8,156,857 B2_

EQUIPMENT FOR THE REHYDRATION OF YEASTS, IN PARTICULAR FOR OENOLOGY

FIELD OF APPLICATION

The present invention concerns improved equipment for the rehydration of yeasts, in particular for oenology, according to the preamble of the main claim.

The equipment of the invention is intended to be advantageously employed in order to provide hydrated and active yeasts adapted for achieving the must fermentation or wine refermentation processes.

STATE OF THE ART

As is known, for the purpose of preservation and facilitated transport, the yeasts employed in the oenological field are generally available in dry or paste form.

The yeast production process conventionally provides for a cell multiplication step, a subsequent dehydration or drying step and finally a generally vacuum packaging step.

The use of the yeasts in dry or paste form in vinification processes therefore requires a step of "revitalisation", aimed at re-establishing the fermentative vigour of the yeasts. Such step must take place in the least traumatic manner possible, so as to prevent compromising the action capacities of the yeasts once inserted in the must (or in the wine), such capacities already in part damaged due to the stress sustained during dehydration.

The revitalisation of the yeasts by means of rehydration must be carried out by taking into account numerous factors, such as the rehydration temperature, the mechanical stresses, the sugar quantity and the quantity of nutritive substances generally to be inserted, the pH, the osmotic pressure etc.

Currently, the rehydration technique most employed in oenology is still of manual use, and provides for the sequential execution of the following operations:

- inserting a measured dose of yeast in a container filled with a quantity of water at a suitable temperature (generally around 40° C.):
- stirring the liquid in order to distribute the yeast;
- waiting out a rehydration period;
- inserting the liquid with the rehydrated yeast in the tubs containing the must to be fermented (or wine to be refermented).

The instructions for achieving this manual rehydration process are generally printed on the same yeast preservation packages present on the market and can contain several variations, including the initial insertion of a certain sugar quantity necessary for the yeast growth.

In practice, such known manual rehydration process of the yeasts has numerous limitations, both operational and functional.

One drawback lies in the manual work required for carrying out the aforesaid operations which can be hard to carry out, especially in the case of high quantities of yeast to be rehydrated, and can require considerable experience by the operator so to prevent subjecting yeasts to shocks that would diminish their effectiveness once inserted in the must (or in the wine).

Hence, the manual rehydration process of the yeasts is not very practical from an operations standpoint and is not always capable of ensuring a satisfactory result from a qualitative standpoint, since it depends on the ability of the operator.

Of course, all the manual operations of the rehydration process require execution times that negatively affect the performance of the entire vinification process.

It should also be considered that yeast rehydration must be carried out to coincide with the grape harvest, i.e. in that period of the year wherein winemaking companies are already subjected to a work overload.

A further limitation of the known manual process of yeast rehydration lies in the impossibility of controlling the parameters which contribute to the rehydration and more in general to the revitalisation of the yeasts themselves.

In fact, in accordance with the prior art, a single initial sugar supply is provided for in the rehydration liquid (generally water).

This represents a clear limitation with regard to the positive outcome of the rehydration process, since it does not allow yeasts to rehydrate and grow in the best conditions. Optimal yeast rehydration in fact requires maintaining a low concentration of sugars dissolved in the water, since excessive glucose concentration leads to the inhibition of yeast respiration, limiting the production of substances necessary for cell functionality. In addition, the rehydration processes of manual type do not allow precisely controlling the water temperature, nor the amount of oxygen dissolved therein, which are instead important parameters for optimal yeast rehydration.

In order to overcome these drawbacks, equipment was recently provided for yeast rehydration, described in the European patent EP-A-1167514, which comprises a containment tank connected with supply source of a rehydration liquid and a supply source of nutritive substances. The equipment provides for circulating the contents of the tank between an inlet thereof and an outlet thereof, having it intercept heating means and insufflation means of a gaseous fluid. The insertion of the liquid in the tank occurs via showering, at least in part, in order to limit the formation of foam.

Such automatic or semi-automatic type solution, while improved with respect to the preceding manual technique, has shown to be not entirely free of drawbacks. In fact, in practice the shower-like fall of the liquid of the recirculation circuit inside the tank does not allow limiting the formation of a considerable amount of foam, due to the surface-active substances produced by the yeasts. Such foam is accumulated atop the surface of the liquid until the partial exit of the liquid is caused from the upper opening of the tank. Furthermore, the excessive foam formation obliges the user to make this equipment work with a reduced yeast load, diminishing therewith the performance of the equipment itself. In order to overcome such drawback, it is known to make this equipment work with a reduced yeast load, diminishing therewith the performance of the equipment itself.

PRESENTATION OF THE INVENTION

The essential object of the present invention is therefore that of eliminating the drawbacks of the art mentioned above by providing equipment for rehydrating yeasts which is capable of ensuring a high oxygen exchange and which ensures, in an economical manner, a high and constant quality standard of yeast rehydration.

A further object of the present invention is that of providing equipment which allows controlling, during the rehydration process, the parameters which contribute in determining the effectiveness of the yeasts once rehydrated.

Another object of the present finding is that of making structurally simple equipment which is entirely reliable in operation.

These objects and still others are achieved by the improved equipment for rehydrating yeasts, in particular for oenology, which comprises:

a containment tank susceptible for receiving a measured dose of dry or paste form yeast to be rehydrated; first supply means for inserting a rehydration liquid in the tank; second supply means for inserting nutritive substances in the tank; a circulation duct placed for connecting between an outlet opening and a return opening of the containment tank, intercepted by pumping means for making the fluid mixture of yeast, rehydration liquid and nutritive substances flow between the openings.

According to the invention, the equipment is characterised in that it comprises means for insufflating air inside the tank which are susceptible for creating an over-pressure of a value which can be set through suitable vent means.

Due to this equipment, it is possible to rehydrate considerable quantities of dry or paste form yeast, considerably diminishing the costs for operator use.

Moreover, such equipment is at the same time structurally simple and entirely reliable in operation.

BRIEF DESCRIPTION OF THE DRAWINGS

The technical characteristics of the finding, according to the aforesaid objects, are clearly seen in the contents of the below-reported claims; the advantages of the same will be more evident in the following description, given with reference to the attached drawing, which represent a merely exemplifying and non-limiting embodiment thereof, wherein:

FIG. 1 shows a logic scheme of the functioning of the equipment for rehydrating yeasts, object of the present invention.

DETAILED DESCRIPTION OF A PREFERRED EMBODIMENT

With reference to the drawing set, the equipment for the yeast rehydration, subject of the present invention, is indicated in its entirety with 1.

As is known in the field of oenology, in vinification processes, dry or paste form yeasts are generally employed which before being inserted in the must to be fermented (or in the wine to be subjected to a refermentation process) must be previously subjected to a rehydration process aimed at reactivating the yeast vigour.

The equipment 1 is capable of actuating the aforesaid rehydration in a substantially automatic manner and for such purpose it comprises a containment tank 2, which is provided with an opening 60 on its upper part through which the yeast to be rehydrated is inserted. Such opening preferably has a size (diameter of about 60 cm) such to allow a facilitated inspection and maintenance inside the tank 2.

In addition, it is closable in a sealed and airtight manner by means of a cover 70.

The tank 2 is hydraulically connected to first supply means 3 for receiving a rehydration liquid, preferably constituted by water, in a controlled manner.

The tank 2 is also furthermore connected to second supply means 4 adapted to insert nutritive substances at its interior for the yeast growth. Such substances conventionally comprise must concentration (MCR), i.e. must with high sugar content obtained by partial elimination of the water. Nevertheless, it is noted below that with the term nutritive substances, it must be intended, without departing from the protective scope of the present patent, both the sugars and the other substances with edaphic or stimulating or regulatory character for the fermentation. Also indicated below, with the term fluid mixture, is the solution composed of the rehydration liquid, yeasts and nutritive substances contained in the tank 2.

In accordance with the embodiment illustrated in the enclosed FIGURE, the first and the second supply means 3, 4 of the water and the nutritive substances have in common a same first pump 5, which is driven by a logic control unit 6 for selectively managing, by means of valves 7, 8 placed on separate suction ducts 9, 10, the supply of different fluids into the tank 2 through a common supply duct 35. The logic control unit 6 manages, also possibly with the aid of (floating) level indicators placed inside the tank 2, the correct quantities of fluids to be inserted inside the tank 2 according to pre-established operating steps which take into account numerous other controlled variables (such as the temperature and oxygenation of the mixture) in order to determine optimal yeast growth. The insertion of the nutritive substances of the rehydration liquid occurs by maintaining the concentration of the sugar which is contained in the nutritive substances themselves within a pre-established value range. The sugar consumption by microorganisms during the re-hydration process is per se known and can be experimentally calculated.

Excessive concentrations of sugars, which can be those of processes which provide for the insertion of the MCR in a single solution at the start of the rehydration process, lead to a deterioration of the effectiveness of the yeasts once rehydrated. In fact, more in particular, unsuitable sugar concentrations do not allow the microorganisms composing the yeasts to produce, in the rehydration process, protective substances of toxic agents such as alcohol, which would allow their greater effectiveness once inserted in the must. More in detail, the aforesaid first pump 5 is in particular of volumetric type with pneumatic actuation, that is, it is composed of another pumping system (such as a peristaltic pump) capable of supplying fluids in a measured manner, and for such purpose is hydraulically connected in delivery by means of a first section 35' to the tank 2 and in suction by means of a second section 35" to the suction ducts 9, 10 in turn adapted to draw from a first and a second container 11, 13 in which water and nutritive substances are respectively stored.

The aforesaid equipment 1 also comprises a circulation duct 14 connected between an outlet opening 15 and one or more return openings 16 of the tank 2, which is intercepted by pumping means constituted by a second pump 17 preferably of centrifuge type, which therefore substantially divide the duct 14 into at least one section upstream 14' and at least one section downstream 14".

According to the idea underlying the present invention, means 32 for insufflating air inside the tank 2 are provided for in order to create over-pressure therein, whose value is regulated by means of suitable vent means 18.

In accordance with the previous regeneration steps of the yeasts managed by the control unit 6, an air flow rate is inserted in the tank which allows an air recirculation inside the tank 2 and an optimal oxygenation of the mixture.

In addition, the over-pressure produced by the air flow advantageously causes a removal of the foam produced by the mixture and permits a high loading of the tank 2 with yeast to be rehydrated.

The vent means 18 allow clearing the air from the tank 2, maintaining an over-pressure here at the desired value and preferably in the range of 100 millibars and 2 bars.

The insufflation of air (or a gaseous mixture with measured concentration can be provided for, for example enriched with oxygen) can be advantageously made by means of a diffuser 19, preferably a sintered porous diffuser in glass, ceramic or steel or in another sinterable material, which micronises the air via atomisation, ensuring perfect diffusion, preferably inside the downstream section 14" of the circulation duct 14.

The air diffuser 19 is advantageously preceded by a filter 33 and by a valve 34 controlled by the control unit 6.

In the embodiment of FIG. 1, the air duct is indicated with dashed lines while the connections with the control unit 6 are indicated with a dash-point line. Conditioning means 20 may also be provided for, actuatable with operating sequences programmed by the logic control unit 6, also as a function of the temperature detected by suitable fluid mixture temperature detection means 21 mounted on the tank 2, these too connected to the logic control unit 6.

The conditioning means 20 are advantageously placed so to intercept the downstream section 14" of the circulation duct 14 and provide for an exchanger 21, wherein the fluid mixture exchanges heat with a fluid vector preferably constituted by water. More in detail, the exchanger 21 is for example of mixture/water type and is selectively supplied with cold water or hot water with respective ducts 36, 37 through valves 22, 23 controlled by the control unit 6, and is connected to an outlet tube 25, it too intercepted by a valve 24.

Preferably, the circulation duct section 14" placed downstream of the centrifuge pump inserts the mixture into the tank 2 by means of two openings 16, 16' placed at the end of respective sections of the duct 14". The first opening 16' is provided for beneath the liquid surface while the second 16 is arranged above the liquid level and in particular above a diffuser 26 adapted to increase the flow surface in contact with the air in order to favour the oxygenation of the mixture.

The latter is laminated on the surface of the diffuser 26, in order to then fall via showering into the tank 2.

Once the rehydration process has terminated, the fluid mixture with the rehydrated yeasts is sent to must and/or wine containment tubs 28 through the discharge means 29 hydraulically connected to the tank 2.

In accordance with a preferential embodiment of the present invention, the discharge means 29 comprise a discharge duct 30 connected to the downstream section 14" of the circulation duct 14 by means of a valve 31.

Of course, the aforesaid equipment is advantageously suited for the rehydration and/or multiplication not only of dry yeasts but also of paste yeasts, in liquid substrate or other form, as well as for the rehydration and/or multiplication of other microorganisms (for example lactic bacteria).

Advantageously, once the yeast rehydration cycle has terminated, the equipment 1 can be subjected to a cleaning step, which will provide for the circulation, inside the equipment 1 (inside the tank, the supple duct 35 and the circulation duct 14), of a detergent fluid drawn from a detergent liquid container preferably by the same first pump 5.

The functioning of the equipment 1 of the invention, described up to now mainly from the structural standpoint, can be better understood as described below.

Initially, the control unit 6 controls the insertion of a quantity of rehydration liquid inside the containment tank 2, of a first measured dose of nutritive substances (including MCR) for the growth of the yeasts through the controlled actuation of the first pump 5 and a measured dose of yeasts through the opening 60.

The rehydration liquid is preferably heated immediately after its insertion in the tank 2 and before the insertion of the yeasts, making it recirculate and thus pass by the conditioning means 20, such that the yeasts subsequently inserted do not incur the danger of undergoing thermal shocks.

At this point, one must wait (normally 20-40 minutes) without stirring the mixture in order to allow the yeasts to be rehydrated.

Afterward, the control unit 6 inserts other doses of nutritive substances inside the tank 2 by controlling the first pump 5.

These steps permit maintaining, in the mixture which formed in the tank 2, a sugar concentration in the pre-established value range.

After having waited for yeast rehydration, the control unit 6 can start the mixing of the mixture through the actuation of the pumping means, which draw the solution from the outlet opening 15 and reinsert it in the tank 2 through the return openings 16 and 16'.

If the temperature probe 27 prearranged in the tank 2 detects a value which is too low, the mixture will be subjected to further heating steps.

After each nutritive substance dose insertion, a waiting step can be provided for in order to allow an optimal rehydration.

Advantageously, the logic control unit 6 can also control the insufflation of air in the mixture, preferably during the circulation of the latter in the circulation duct 14.

Several insertions of different rehydration liquid quantities into the containment tank 2 can also be provided for.

As is known, the rehydrated yeasts can be employed either for the fermentation on must or for refermentation on wine, if one wishes to obtain sparkling or spumante wines, or if one wishes to exhaust the sugar supply.

Of course, according to the finding all the above-described operations will be automatically controlled by the logic control unit 6, which can be programmed as a function of the different needs and in particular of the type of yeast and must and/or wine to be fermented.

The finding thus conceived therefore attains the pre-established objects.

Of course, in its practical achievement it can assume forms and configurations which are different from those illustrated above, without departing from the present protective scope. Moreover, all details can be substituted with technically equivalent elements and the sizes, shapes and materials used can be of any type as needed.

The invention claimed is:

1. Improved equipment for yeast rehydration, in particular for oenology, which comprises:
    a containment tank (2) susceptible for receiving a measured dose of yeast in dry or paste form to be rehydrated;
    first supply, device (3) adapted to insert a rehydration liquid in said tank;
    second supply device (4) adapted to insert nutritive substances in said tank;
    wherein said yeast, said rehydration liquid and said nutritive substances form a fluid mixture;
    at least one circulation duct (14) placed in connection between at least one outlet opening (15) and at least one return opening (16, 16') of said containment tank (2), intercepted by a pumping device (17) for making said fluid mixture flow between said openings (15, 16);
    wherein said equipment further comprises an air insufflating device for insufflating air (32) inside said tank (2) which insufflating device is actuatable independently of said pumping device (17) for the circulation of said fluid mixture in said circulation duct (14) and is susceptible for creating an over-pressure of a value that can be set through a vent (18),
    wherein said air insufflating device is actuatable independently of said pumping device for the circulation of said fluid mixture in said circulation duct (14); and
    said vent (18) allows clearing of air from the tank, maintaining said over-pressure at a desired value.

2. Improved equipment for yeast rehydration according to claim 1, characterised in that said tank (2) is provided with an opening (60) on its upper part, which is closable in a sealed and airtight manner by means of a cover (70).

3. Improved equipment for yeast rehydration according to claim 1, characterised in that the return opening (16) of said circulation duct (14) distributes the flow of said fluid mixture inside said tank (2) above a diffuser (26) adapted to increase the surface area of the flow in contact with the air, so to favour the oxygenation of the mixture.

4. Improved equipment for yeast rehydration according to claim 1, characterised in that said air insufflation device (32) comprise an air diffuser (19) adapted to atomise an air flow rate inside the mixture.

5. Improved equipment for yeast rehydration according to claim 4, characterised in that said air diffuser (19) is placed so to intercept said circulation duct (14).

6. Improved equipment for yeast rehydration according to claim 1, characterised in that said over-pressure is in the range of 100 millibars and 2 bars.

7. Improved equipment for yeast rehydration according to claim 1, comprising a programmable logic control unit (6) adapted to control said first and said second supply devices (3, 4), said air insufflation device (32) in order to subject said mixture to pre-established regeneration conditions in accordance with the rehydration liquid, nutritive substances and dissolved gas requirement.

8. Improved equipment for yeast rehydration according to claim 7, comprising conditioning means (20) activatable with operating sequences programmed by said logic control unit (6) as a function of the temperature detected by at least one temperature detection probe (27) of said mixture connected with said logic control unit (6).

9. Improved equipment for yeast rehydration according to claim 1, characterised in that said second supply device (4) of nutritive substances comprise a second container (13) of nutritive substances connected with said containment tank (2) by a supply duct (35) operatively associated with at least a first pump (5).

10. Improved equipment for yeast rehydration according to claim 1, characterised in that said first and/or second supply devices (3, 4) comprise a volumetric pump (5).

11. Improved equipment for yeast rehydration according to claim 1, characterised in that said circulation duct (14) is provided with at least one return opening (16') beneath the surface of the liquid in said tank (2).

12. Improved equipment for yeast rehydration according to claim 1, comprising discharge means (29) hydraulically connected to said containment tank (2) in order to send said mixture to at least one containment tub (28) of must or wine.

13. Improved equipment for yeast rehydration according to claim 12, characterised in that said discharge means (29) comprise a discharge duct (30) connected to said circulation duct (14) and intercepted by a valve (31).

14. Improved equipment for yeast rehydration according to claim 9, characterised in that said first supply device (3) of nutritive substances comprise a first container (11) of a rehydration liquid connected to said containment tank (2) by a supply duct (35) operatively associated with at least a first pump (5).

15. Improved equipment for yeast rehydration according to claim 14, characterised in that said supply duct (35) is connected through suction ducts (9, 10) intercepted by valves (7, 8) to said first and second container (11, 13) in which the rehydration liquid and the nutritive substances are respectively stored.

\* \* \* \* \*